(12) United States Patent
Carter

(10) Patent No.: US 11,083,391 B2
(45) Date of Patent: Aug. 10, 2021

(54) ELECTRODE IMPEDANCE SPECTROSCOPY

(75) Inventor: Paul Carter, West Pennant Hills (AU)

(73) Assignee: Cochlear Limited, Macquarie University (AU)

(*) Notice: Subject to any disclaimer, the term of this patent is extended or adjusted under 35 U.S.C. 154(b) by 2037 days.

(21) Appl. No.: 13/158,042

(22) Filed: Jun. 10, 2011

(65) Prior Publication Data

US 2012/0316454 A1 Dec. 13, 2012

(51) Int. Cl.
| | |
|---|---|
| *A61F 2/18* | (2006.01) |
| *A61B 5/053* | (2021.01) |
| *A61F 11/04* | (2006.01) |
| *A61N 1/02* | (2006.01) |
| *A61N 1/05* | (2006.01) |
| *A61N 1/372* | (2006.01) |
| *H04R 25/00* | (2006.01) |
| *A61B 5/00* | (2006.01) |
| *A61N 1/36* | (2006.01) |

(52) U.S. Cl.
CPC ............... *A61B 5/053* (2013.01); *A61F 2/18* (2013.01); *A61F 11/04* (2013.01); *A61N 1/025* (2013.01); *A61N 1/0541* (2013.01); *A61N 1/37229* (2013.01); *H04R 25/505* (2013.01); *H04R 25/604* (2013.01); *A61B 5/7264* (2013.01); *A61F 2002/183* (2013.01); *A61F 2240/008* (2013.01); *A61N 1/36038* (2017.08); *A61N 1/36039* (2017.08); *H04R 2225/67* (2013.01)

(58) Field of Classification Search
CPC .. A61N 1/36032; A61B 5/053; A61B 5/0537; A61B 5/4872

USPC .......................................................... 600/547
See application file for complete search history.

(56) References Cited

U.S. PATENT DOCUMENTS

| | | | | |
|---|---|---|---|---|
| 4,782,284 | A | * 11/1988 | Adams ..................... | G01H 7/00 324/76.15 |
| 5,282,840 | A | * 2/1994 | Hudrlik .................. | A61B 5/053 600/547 |
| 5,603,726 | A | * 2/1997 | Schulman et al. ............. | 607/57 |
| 5,626,629 | A | * 5/1997 | Faltys et al. .................... | 607/57 |
| 5,818,215 | A | * 10/1998 | Miyamae ............. | G01R 23/173 324/76.27 |
| 5,876,425 | A | | 3/1999 | Gord et al. |

(Continued)

FOREIGN PATENT DOCUMENTS

| | | | |
|---|---|---|---|
| EP | 1754509 | * | 2/2007 |
| EP | 2113283 | | 11/2009 |

(Continued)

OTHER PUBLICATIONS

Machine translated version of EP 1754509 (see above). Translated on Sep. 29, 2014 by Espacenet.*

(Continued)

*Primary Examiner* — Daniel L Cerioni
(74) *Attorney, Agent, or Firm* — Piloff Passino & Cosenza LLP; Martin J. Cosenza

(57) ABSTRACT

Aspects of the present invention are generally directed to impedance spectroscopy in an active implantable medical device (AIMD) comprising a component with one or more electrodes. In an embodiment, the AIMD applies a signal at a plurality of frequencies using one or more of the electrodes. Measurements are then obtained for the applied signal to determine impedance(s) at the applied frequencies of the tissue in which the electrodes are located.

48 Claims, 9 Drawing Sheets

(56) References Cited

U.S. PATENT DOCUMENTS

| | | | |
|---|---|---|---|
| 6,882,879 B2 | 4/2005 | Rock | |
| 6,968,229 B2* | 11/2005 | Siemons | A61B 5/0534 33/513 |
| 7,430,546 B1* | 9/2008 | Suri | G06N 3/08 706/16 |
| 7,650,183 B2 | 1/2010 | Rock | |
| 8,265,766 B1* | 9/2012 | Kulkarni et al. | 607/56 |
| 8,532,781 B1* | 9/2013 | Vanpoucke | A61N 1/37247 607/57 |
| 2001/0049466 A1 | 12/2001 | Leysieffer et al. | |
| 2004/0133122 A1* | 7/2004 | Pearlman | A61B 5/0536 600/547 |
| 2004/0138723 A1 | 7/2004 | Malick et al. | |
| 2006/0235500 A1 | 10/2006 | Gibson et al. | |
| 2007/0100666 A1* | 5/2007 | Stivoric | G01R 29/0814 705/3 |
| 2007/0282397 A1 | 12/2007 | Ball et al. | |
| 2009/0219193 A1* | 9/2009 | Szajnowski | G01S 13/282 342/128 |
| 2010/0041940 A1* | 2/2010 | Hillbratt | H04R 25/606 600/25 |
| 2010/0106047 A1* | 4/2010 | Sarfaty | A61B 5/05 600/547 |
| 2010/0114288 A1* | 5/2010 | Haller | A61B 17/3468 607/137 |
| 2011/0087085 A1 | 4/2011 | Tsampazis et al. | |
| 2011/0144510 A1* | 6/2011 | Ryu | A61B 5/042 600/509 |
| 2011/0264165 A1* | 10/2011 | Molnar | A61N 1/36185 607/45 |
| 2011/0306867 A1* | 12/2011 | Gopinathan | A61B 5/02007 600/407 |
| 2012/0286765 A1* | 11/2012 | Heuvel | H04R 25/606 324/76.49 |

FOREIGN PATENT DOCUMENTS

| | | |
|---|---|---|
| WO | WO-2009/124287 | 10/2009 |
| WO | WO-2009/136157 | 11/2009 |
| WO | WO-2010/025517 | 3/2010 |

OTHER PUBLICATIONS

English translation of EP patent 1 754 509 to Bousack et al. Translation provided by ProQuest on May 18, 2015.*
International Search Report and Written Opinion for International Application No. PCT/IB2012/052917 dated Jan. 21, 2013 (10 pages).
Duan, et al., "A Study of intra-cochlear electrodes and tissue interface by electrochemical impedance methods in vivo", *Biomaterials*, vol. 25, Issue 17, Aug. 2004. pp. 3813-3828.
Williams, Justin C. et al., "Complex impedance spectroscopy for monitoring tissue responses to inserted neural implants", *J. Neural Eng.* vol. , Nov. 27, 2007, pp. 410-423.
Supplemental European Search Report and Opinion for EP 12 79 6080, dated Jan. 16, 2015.

* cited by examiner

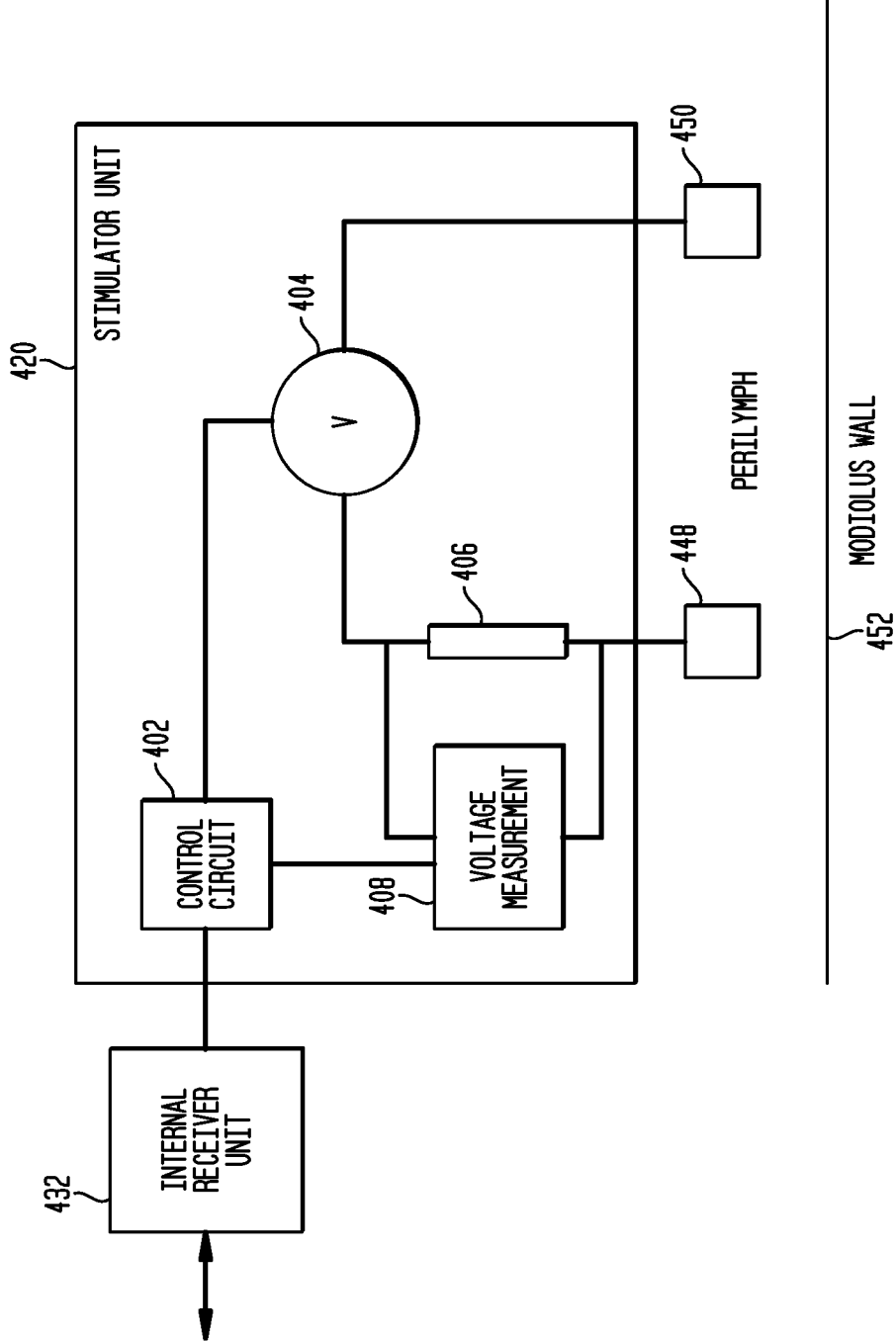

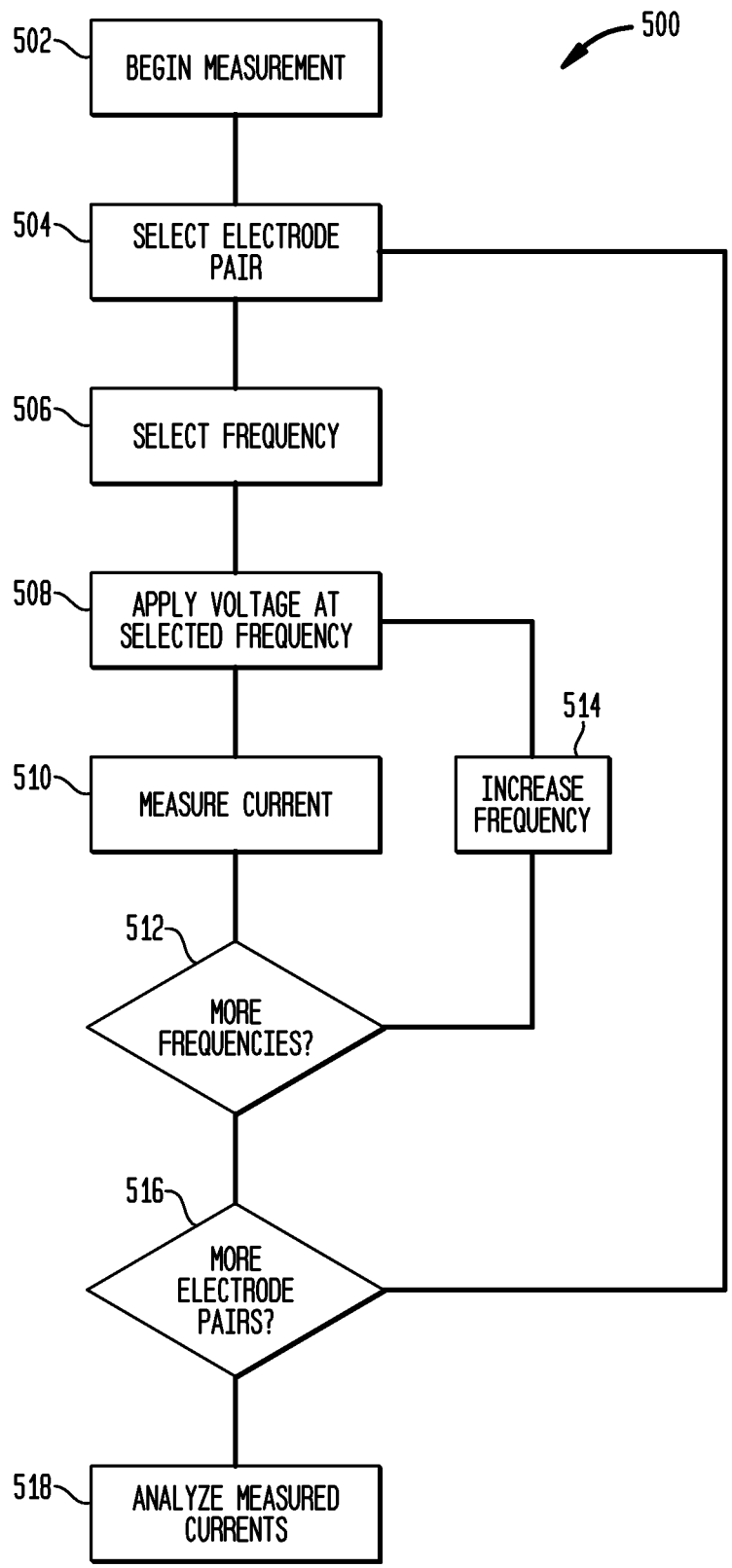

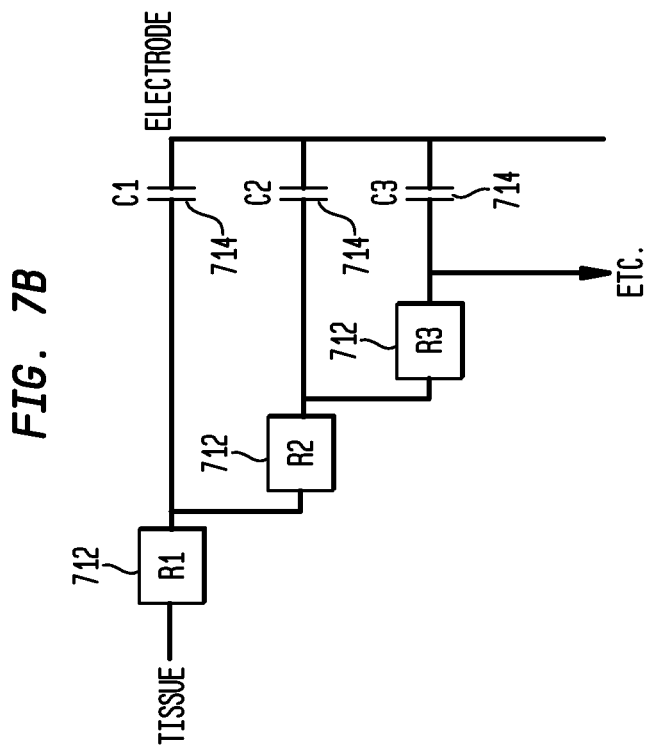
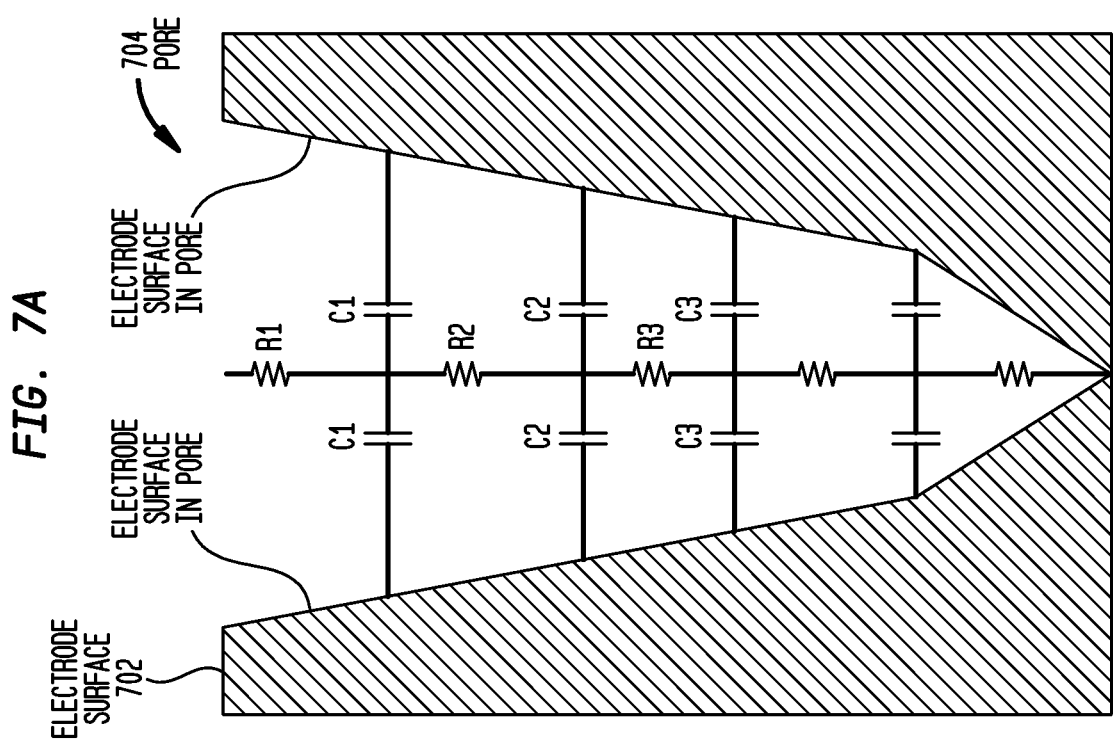

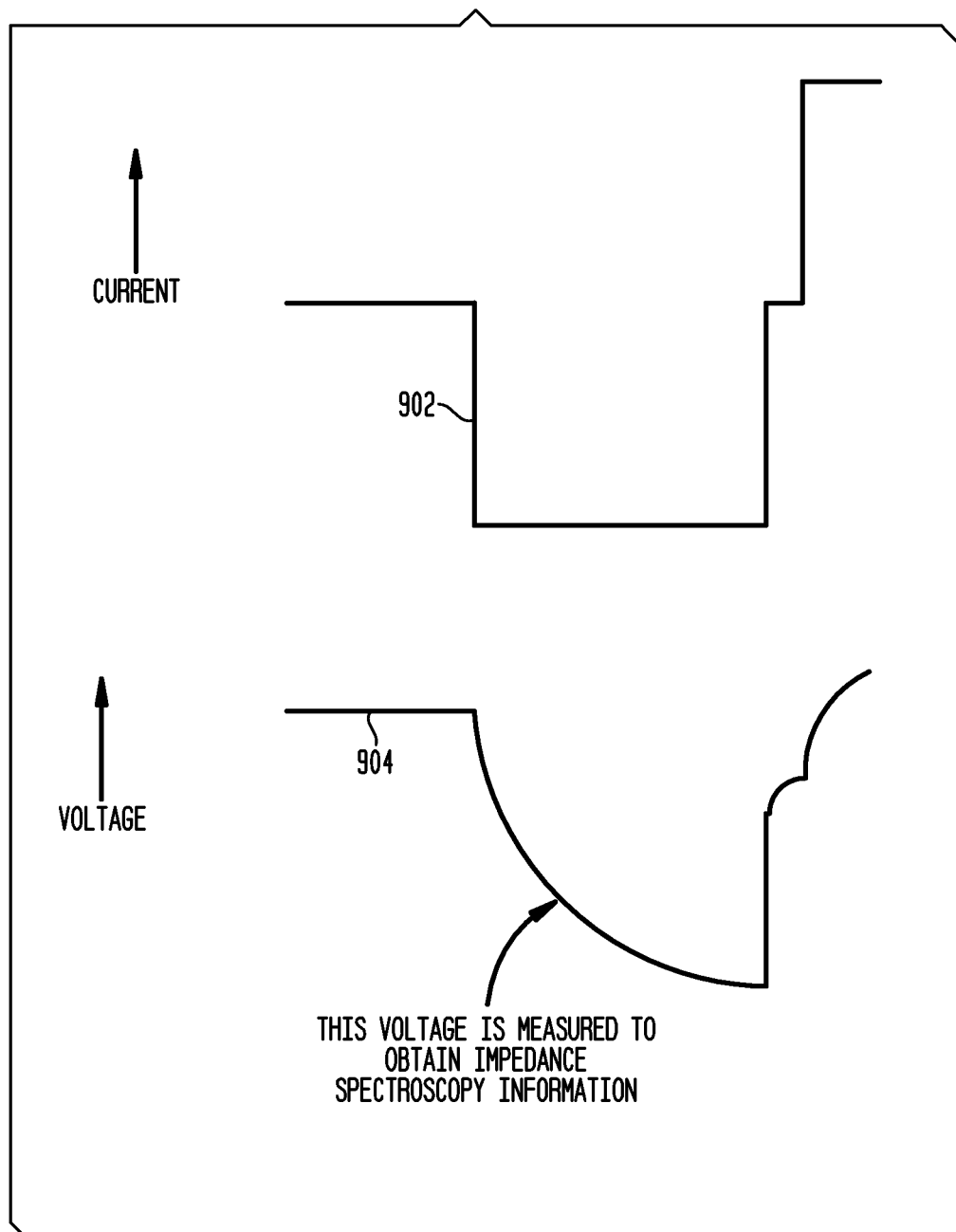

ELECTRODE IMPEDANCE SPECTROSCOPY

BACKGROUND

Field of the Invention

The present invention relates generally to implantable stimulator systems, and more particularly, to impedance measurements in an implantable stimulator system.

Related Art

Implantable medical devices have provided benefits to recipients over recent decades. Implantable medical devices are devices having one or more components or elements that are at least partially implantable in a recipient. One type of implantable medical device is an active implantable medical device (AIMDs), which are medical devices having one or more implantable components that rely for their functioning upon a source of power other than the human body or gravity, such as an electrical energy source. Exemplary AIMDs include devices configured to provide one or more of stimulation and sensing, such as implantable stimulator systems and implantable sensor systems.

Implantable stimulator systems provide stimulation to a recipient of the device. Exemplary implantable stimulator systems include, but are not limited, to cochlear implants, auditory brain stem implants, cardiac pacemakers, neurostimulators, functional electrical stimulation (FES) systems, etc.

Cochlear implants include an electrode assembly implanted in the cochlea and are used to treat sensorineural hearing loss. Electrical stimulation signals are delivered directly to the auditory nerve via the electrode assembly, thereby inducing a hearing sensation in the implant recipient.

An Auditory Brain Stem Implants (ABI) is another type of surgically implanted electronic device that provides a sense of sound to a recipient suffering from sensorineural hearing loss. ABIs are typically used in recipients suffering from sensorineural hearing loss that, due to damage to the recipient's cochlea or auditory nerve, are unable to use a cochlear implant.

A cardiac pacemaker is a medical device that uses electrical impulses, delivered by electrodes contacting the heart muscles, to regulate the beating of a heart. The primary purpose of a pacemaker is to maintain an adequate heart rate.

A neurostimulator, also sometimes referred to as an implanted pulse generator (IPG) is a battery powered device designed to deliver electrical stimulation to the brain. Neurostimulators are sometimes used for deep brain stimulation and vagus nerve stimulation to treat neurological disorders.

FES uses electrical currents to activate nerves innervating extremities affected by paralysis resulting from, for example, spinal cord injury, head injury, stroke, or other neurological disorders.

Other types of implantable stimulator systems include systems configured to provide electrical muscle stimulation (EMS), also known as neoromuscular stimulation (NMES) or electromyostimulation, which involves the application of electric impulses to elicit muscle contraction.

Exemplary implantable sensor systems include, but are not limited to, sensor systems configured to monitor cardiac, nerve and muscular activity.

SUMMARY

In one aspect of the invention, there is provided a method of operating an active implantable medical device (AIMD) comprising an electrode, the method comprising: applying a measurement signal at a plurality of frequencies to a recipient of the AIMD using the electrode; and performing, using the AIMD, a measurement, responsive to the measurement signal and indicative of an impedance of the electrode and tissue of the recipient, at each of the plurality of frequencies.

In another aspect, there is provided an active implantable medical device comprising: a component comprising an electrode; a signal generator configured to apply a signal using the electrode at a plurality of frequencies; and a control circuit configured to perform a measurement, responsive to the signal, indicative of an impedance of the electrode and tissue of the recipient for each of the plurality of frequencies.

In yet another aspect, there is provided a system for performing spectroscopy comprising: an active implantable medical device (AIMD) comprising: an electrode; means for applying a measurement signal to a recipient using the electrode at a plurality of frequencies; and means for performing, using the AIMD, a measurement, responsive to the measurement signal and indicative of an impedance of the electrode and tissue of the recipient for each of the plurality of frequencies.

BRIEF DESCRIPTION OF THE DRAWINGS

Illustrative embodiments of the present invention are described herein with reference to the accompanying drawings, in which:

FIG. 4 provides a simplified diagram of exemplary circuitry for impedance spectroscopy in a cochlear implant, in accordance with an embodiment of the present invention;

FIG. 5 is a flow chart of an exemplary 500 for obtaining impedance measurements, in accordance with an embodiment of the present invention;

FIG. 7A provides a diagram for illustrating how the uneven surface of an electrode at the microscopic level can be modeled as a CPE;

FIG. 7B provides a diagram of a circuit model for a CPE in accordance with FIG. 7A;

FIG. 9 illustrates a square wave current pulse and a resulting measured voltage 904, in accordance with an embodiment of the present invention.

DETAILED DESCRIPTION

Embodiments of the present invention are generally directed to impedance spectroscopy in an active implantable medical device (AIMD) comprising a component with one or more electrodes. In an embodiment, the AIMD applies a signal at a plurality of frequencies using one or more of the electrodes. Measurements are then taken for the applied signal. These measurements are used to measure impedance(s) at the applied frequencies of the tissue in which the electrodes are located. The measured impedances are then analyzed to determine, for example, the proximity of the electrodes to one or more biological structures of the recipient. This information may be used by a surgeon during implantation of the component of the AIMD in the recipient or by a clinician at any time to diagnose potential problems with or to confirm correct operation of one or more electrodes of the AIMD or the tissue surrounding them.

Embodiments of the present invention are described herein primarily in connection with one type of Active Implantable Medical Device (AIMD), namely a cochlear implant system (commonly referred to as cochlear prosthetic devices, cochlear prostheses, cochlear implants, cochlear devices, and the like; simply "cochlea implant systems" herein.) Cochlear implant systems generally refer to hearing prostheses that deliver electrical stimulation to the cochlea of a recipient. As used herein, cochlear implant systems also include hearing prostheses that deliver electrical stimulation in combination with other types of stimulation, such as acoustic or mechanical stimulation. It would be appreciated that embodiments of the present invention may be implemented in other types of AIMDs.

Figure 1:
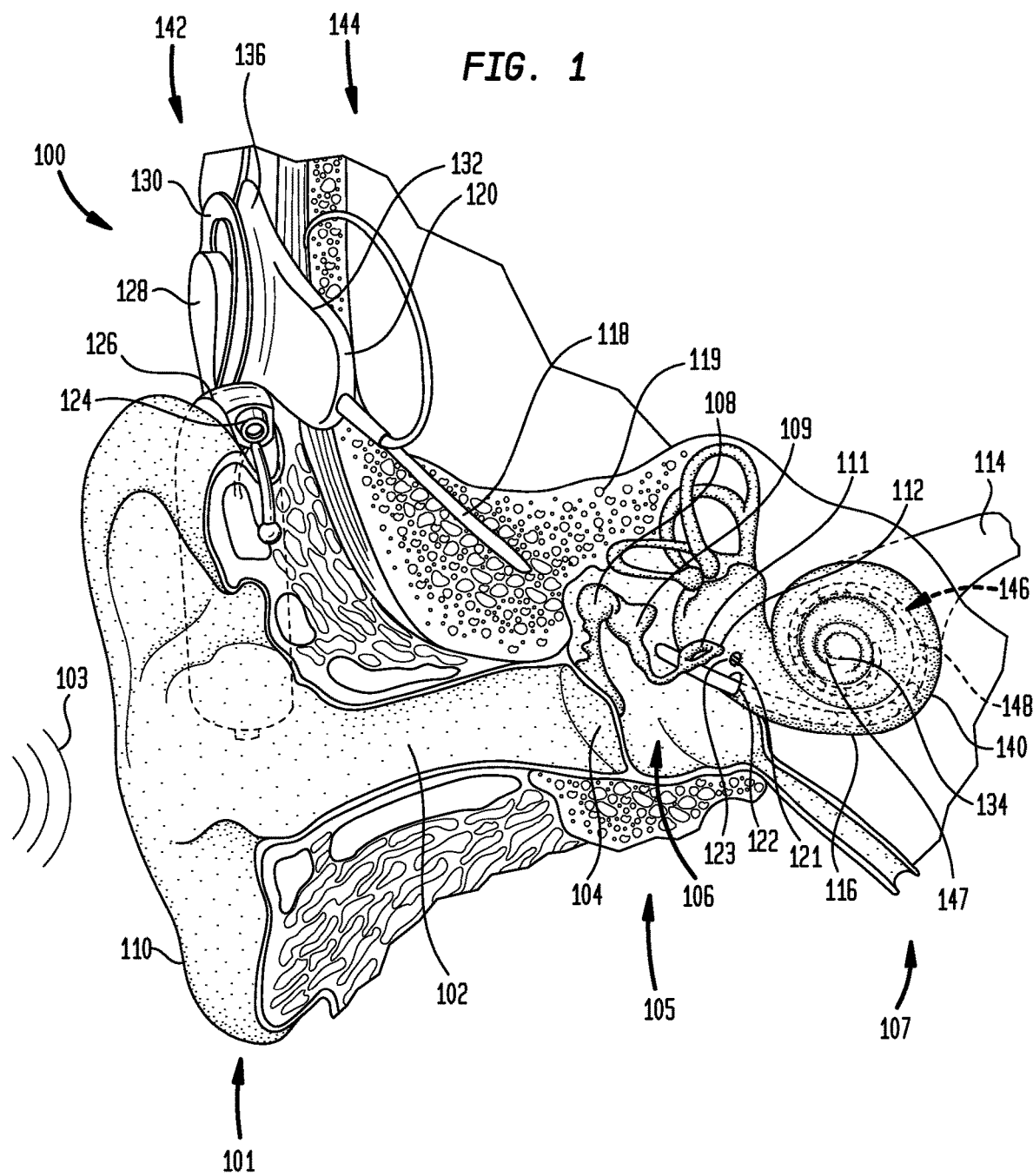
FIG. 1 is a perspective view of a cochlear implant system in which embodiments of the present invention may be implemented.
Figure 2:
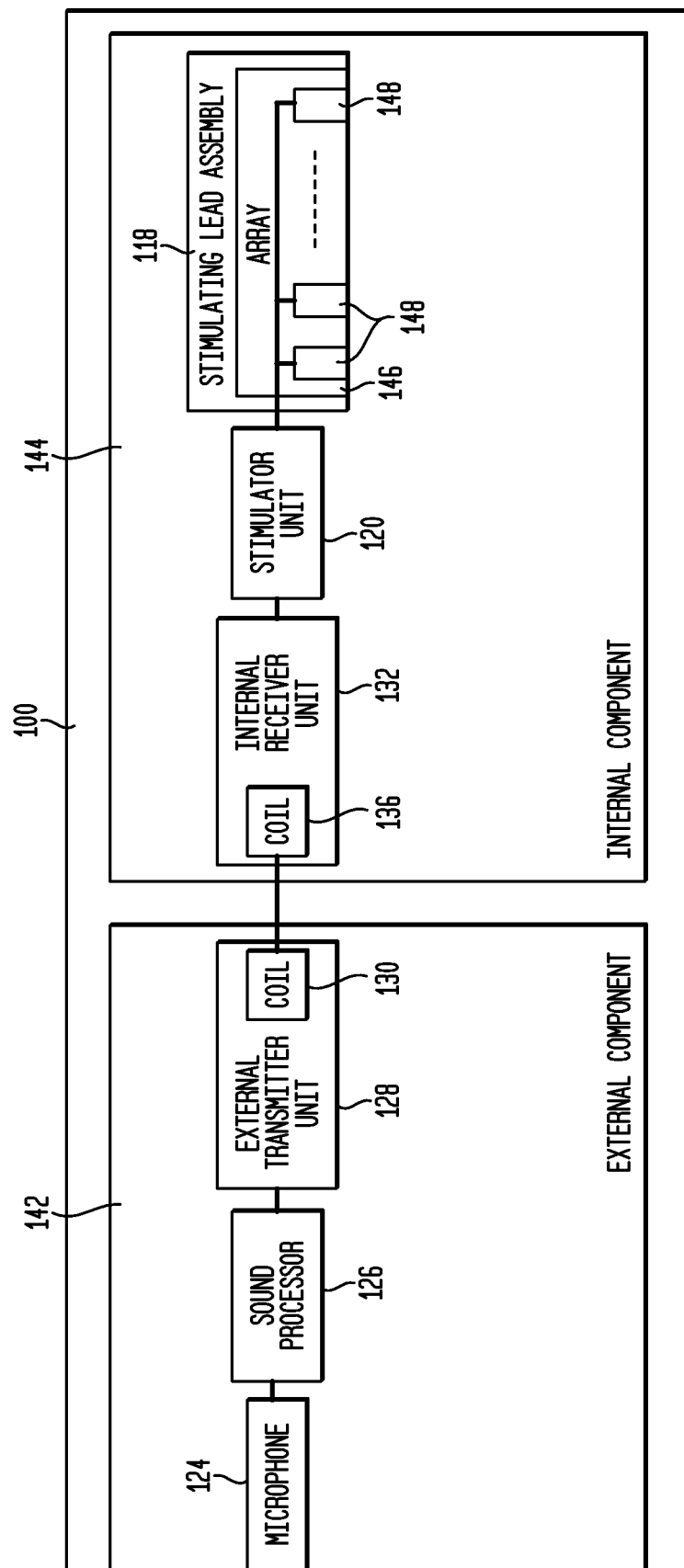
FIG. 2 is a functional block diagram of the cochlear implant system of FIG. 1, in accordance with an embodiment of the present invention.

FIG. 1 is perspective view of a cochlear implant system, referred to as cochlear implant system 100 implanted in a recipient. FIG. 2 is a functional block diagram of cochlear implant system 100. The recipient has an outer ear 101, a middle ear 105 and an inner ear 107. Components of outer ear 101, middle ear 105 and inner ear 107 are described below, followed by a description of cochlear implant system 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear cannel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

Cochlear implant system 100 comprises an external component 142 which is directly or indirectly attached to the body of the recipient, and an internal component 144 which is temporarily or permanently implanted in the recipient. External component 142 typically comprises one or more sound input elements, such as microphone 124 for detecting sound, a sound processor 126, a power circuit (not shown), and an external transmitter unit 128. External transmitter unit 128 comprises an external coil 130 and, preferably, a magnet (not shown) secured directly or indirectly to external coil 130. Sound processor 126 processes the output of microphone 124 that is positioned, in the depicted embodiment, by auricle 110 of the recipient. Sound processor 126 generates encoded signals, sometimes referred to herein as encoded data signals, which are provided to external transmitter unit 128 via a cable (not shown). Sound processor 126 may further comprise a data input interface (not shown) that may be used to connect sound processor 126 to a data source, such as a personal computer or musical player (e.g., an MP3 player).

Internal component 144 comprises an internal receiver unit 132, a stimulator unit 120, and a stimulating lead assembly 118. Internal receiver unit 132 comprises an internal coil 136, and preferably, a magnet (also not shown) fixed relative to the internal coil. Internal receiver unit 132 and stimulator unit 120 are hermetically sealed within a biocompatible housing, sometimes collectively referred to as a stimulator/receiver unit. The internal coil receives power and stimulation data from external coil 130. Stimulating lead assembly 118 has a proximal end connected to stimulator unit 120, and a distal end implanted in cochlea 140. Stimulating lead assembly 118 extends from stimulator unit 120 to cochlea 140 through mastoid bone 119. In some embodiments stimulating lead assembly 118 may be implanted at least in basal region 116, and sometimes further. For example, stimulating lead assembly 118 may extend towards apical end of cochlea 140, referred to as cochlea apex 134. In certain circumstances, stimulating lead assembly 118 may be inserted into cochlea 140 via a cochleostomy 122. In other circumstances, a cochleostomy may be formed through round window 121, oval window 112, promontory 123 or through an apical turn 147 of cochlea 140.

Stimulating lead assembly 118 comprises a longitudinally aligned and distally extending array 146 of electrodes 148 (also referred to as electrode contacts), sometimes referred to as array of electrodes 146 or array of electrode contacts 146 herein. Although array of electrodes 146 may be disposed on stimulating lead assembly 118, in most practical applications, array of electrodes 146 is integrated into stimulating lead assembly 118. As such, array of electrodes 146 is referred to herein as being disposed in stimulating lead assembly 118. Stimulator unit 120 generates stimulation signals which are applied by electrodes 148 to cochlea 140, thereby stimulating auditory nerve 114. Because, in cochlear implant system 100, stimulating lead assembly 118 provides stimulation, stimulating lead assembly 118 is sometimes referred to as a stimulating lead assembly. Stimulator unit 120 may further be connected to an extra-cochlear electrode (not shown) located external to the recipient's cochlea 140.

In cochlear implant system 100, external coil 130 transmits electrical signals (that is, power and stimulation data) to internal coil 136 via a radio frequency (RF) link. Internal coil 136 is typically a wire antenna coil comprised of multiple turns of electrically insulated single-strand or multi-strand platinum or gold wire. The electrical insulation of internal coil 136 is provided by a flexible silicone molding (not shown). In use, implantable receiver unit 132 may be positioned in a recess of the temporal bone adjacent auricle 110 of the recipient.

Figure 3A:
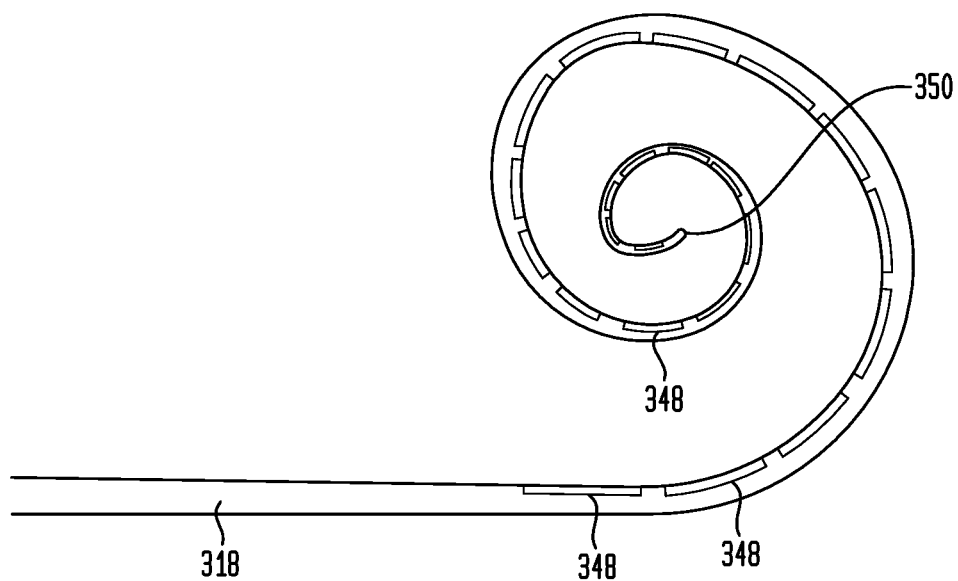
FIG. 3A is a simplified diagram of an exemplary stimulating lead assembly, in accordance with an embodiment of the present invention.
Figure 3B:
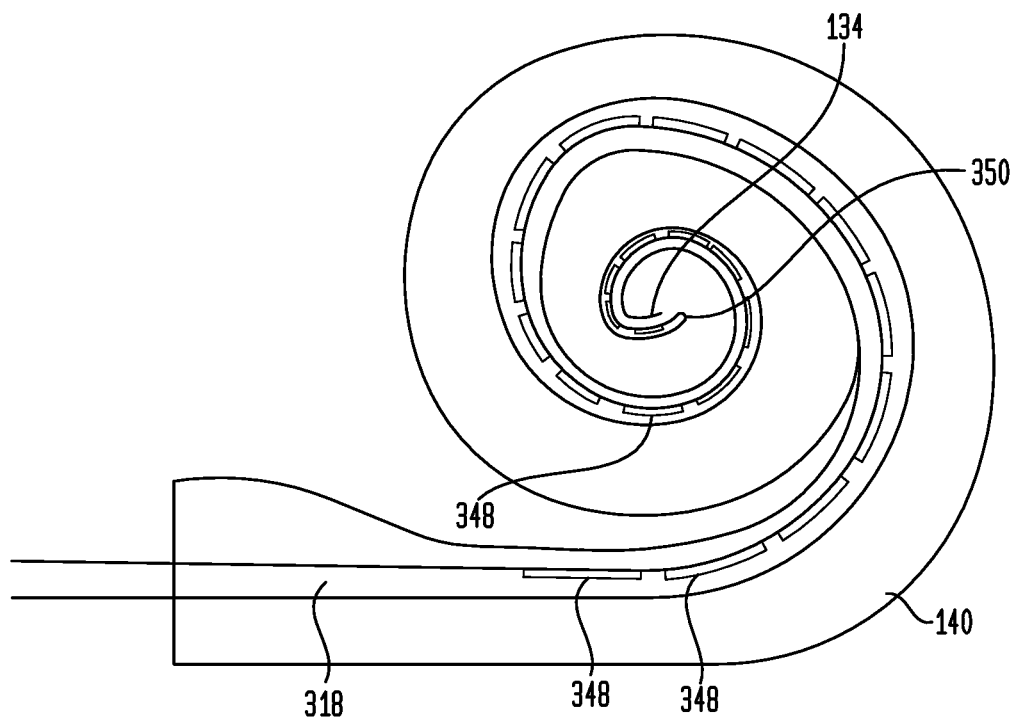
FIG. 3B illustrates the stimulating lead assembly of FIG. 3A inserted in a cochlea.

FIG. 3A is a simplified diagram of an exemplary stimulating lead assembly 318, in accordance with an embodiment of the present invention. FIG. 3B illustrates stimulating lead assembly 318 inserted in cochlea 140. As illustrated, stimulating assembly 318 is configured to adopt a curved configuration during and or after implantation into the recipient's cochlea 140. To achieve this, in certain embodiments, stimulating assembly 318 is pre-curved to the same general curvature of a recipient's cochlea 140. In such embodiments, stimulating assembly 318 is sometimes referred to as perimodiolar stimulating assembly where stimulating assembly 318 adopts its curved configuration in cochlea 140. When implanted, the surface of stimulating lead assembly 318 that faces the interior of cochlea 140 is referred to herein as the medial surface of stimulating lead assembly 318. As illustrated, electrodes 348 are located on the medial side of stimulating lead assembly 318. Further, as shown, when implanted the tip 350 of stimulating lead assembly 318 is located near the cochlear apex 134.

Although FIGS. 3A-3B illustrate a perimodiolar stimulating assembly. In other embodiments, stimulating assembly may be a non-perimodiolar stimulating assembly which does not adopt a curved configuration. For example, stimulating assembly 318 may comprise a straight stimulating assembly or a mid-scala assembly which assumes a mid-scala position during or following implantation. In further embodiments, cochlear implant could include a stimulating assembly implantable into a natural crevice in the cochlea that allows for the hydrodynamic nature of the cochlea to be maintained, or an assembly positioned adjacent to the cochlea.

The state of the tissue and anatomical structures surrounding the electrodes of a stimulating lead assembly is typically an important factor with regard to the effectiveness of stimulation delivered to the recipient. Present stimulator systems measure the impedance of each electrode, which provides a useful measure that assists clinicians in diagnosing faults, assessing the position of the electrode and determining anatomical anomalies in the cochlea. This impedance is currently reported as a single number and thus provides limited information about the state of the tissue surrounding the electrode. For example, this impedance is typically determined at what is essentially a single frequency and used for the limited purpose of fault detection in cochlear implants.

As will be discussed further below, an embodiment of the present invention, measures the impedance of an electrode and its surrounding tissue over a range of frequencies (referred to herein as impedance spectroscopy) to obtain a more detailed picture of the state of the electrode and its surrounding tissue (including the surrounding anatomical structures).

These impedance measurements may be used in a plurality of applications. For example, these impedance measurements may be used to determine the proximity of an electrode to different physical structures (e.g., the modiolus, the lateral wall, etc.) within the cochlea since different physical structures may present different spectroscopic signatures. This information may be used during surgical implantation, for example, to provide the surgeon with information regarding the position of the stimulating lead assembly in the recipient's cochlea. For example, this information may be used to determine the instantaneous insertion depth of the stimulating lead assembly 318. Further, post surgery, this information (e.g., the proximity of the electrodes to the modiolus) may be useful in predicting performance of the cochlear implant.

Impedance spectroscopy in accordance with embodiments of the present invention may also be useful in detecting issues with the tissue surrounding the stimulating lead assembly, such as assessing the extent of scar tissue around the electrodes or the presence of an infection near the electrode. Additionally, during surgical implantation impedance spectroscopy in accordance with embodiments may be useful in detecting tip fold-over (i.e., when tip 350 folds back on stimulating lead assembly 318 during the insertion process). Impedance spectroscopy in accordance with embodiments may also be useful in detecting other stimulating lead assembly faults (e.g., faults more complex than simple open circuits or short circuits) as will be discussed in more detail below.

As noted above, an embodiment measures the impedance of an electrode and its surrounding tissue over a range of frequencies to obtain a more detailed picture of the state of the electrode and its surrounding tissue (including the surrounding anatomical structures). In an embodiment, these impedances are measured by measuring the impedance between a pair of electrodes (e.g., an electrode of the stimulating lead assembly and an extra-cochlear electrode) of a stimulating lead assembly over the frequency range. The measurements may be used to generate impedance spectroscopy plots. The characteristics of the tissue close to the electrodes can have a significant impact on the measured impedances, and thus the shape of generated impedance spectroscopy plots. For example, the close proximity of the modiolar wall to the electrode may have a profound effect on the shape of the plot compared to the plot's shape when the electrode is surrounded by perilymph, the fluid which occupies the space inside the cochlea 140. Thus, a plot of measurements when the electrode is near the modiolus will look quite different from a plot of measurements taken when the electrode is distant from it and surrounded by perilymph. As will be discussed further below, an embodiment of the present invention uses impedance spectroscopy to obtain an impedance spectroscopy plot and then compares the obtained plot with different characteristic plot shapes to obtain information regarding the stimulating lead assembly, such as, for example, the proximity of the electrode(s) to various cochlear structures, characteristics of the tissue surrounding the electrode(s), issues with the stimulating lead assembly (e.g., tip fold-over, faults, etc.).

FIG. 4 provides a simplified diagram of exemplary circuitry for impedance spectroscopy in a cochlear implant, in accordance with an embodiment of the present invention. For ease of explanation only the components discussed below are illustrated in FIG. 4. As illustrated, stimulator unit 420 is connected to internal receiver unit 432, electrode 448 and extra-cochlear electrode 450. Stimulator unit 420, internal receiver unit 432, electrode 448, extra-cochlear electrode 450 may be, for example, components such as the correspondingly named stimulator unit 120, internal receiver unit 132, electrode 148 and extra-cochlear electrode (not shown) discussed above with reference to FIGS. 1-2.

As illustrated, stimulator unit 420, includes a control circuit 402, a signal generator 404, a resistor 406, and a voltage measurement circuit 408. Control circuit 402 may be a circuit (e.g., an Application Specific Integrated Circuit (ASIC)) configured for exercising control over the stimulator unit 420. For example, control circuit 402 may be configured for receiving, from the internal receiver unit 432, the encoded data signals regarding the sound and generating the stimulating signals for applying stimulation via electrodes 448 and 450.

Signal generator 404 generates a voltage for application via the stimulating lead assembly. For ease of explanation, signal generator 404 is a separate voltage generator distinct from the electronics used for applying stimulation to cause a hearing percept by the recipient. It should be noted that FIG. 4 provides but one simple example of an embodiment for performing impedance spectroscopy in accordance with the present invention and that in other embodiments other types of systems and components may be used. For example, as will be discussed further below, another embodiment uses the existing current generator present in typical cochlear implants for generating the signal in place of the voltage generator used in the embodiment of FIG. 4.

As illustrated, a voltage measurement circuit 408 is connected to opposite ends of resistor 406. Resistor 406 may be a standard resistor, such as, for example, a 100 ohm resistor. Voltage measurement circuit 408 may include any type of circuitry configured to output a signal indicative of the voltage across resistor 406. For example, in an embodiment, voltage measurement circuit 408 may comprise a differential amplifier that takes as inputs the signals on opposite sides of resistor 406 and then amplifies the difference in the voltage between the two sides. Voltage measurement circuit 408 provides the measured voltage to control circuit 402. Further, in embodiments, voltage measurement circuit 408 may comprise an analog to digital converter (ADC) that digitizes the measured voltage before providing the measured voltage to the control circuit 402.

FIG. 5 provides a flow chart of an exemplary method 500 for obtaining impedance measurements, in accordance with an embodiment of the present invention. Control circuit 402, at block 502, initiates the process for measuring impedances. In an embodiment, the process is performed during surgical implantation to obtain information regarding the location of the stimulating lead assembly in the recipient's cochlea during the surgical implantation procedure. In such an embodiment, the electrode(s) of the stimulating lead assembly may be connected to an external device configured to aid the surgeon during the implantation process. In the illustrated embodiment of FIG. 4, the external device may be, for example, connected to the sound processor 126 (FIG. 1), connected to the internal receiver unit 132, or connected to the stimulator unit 120. In such examples, the connection between the external device and the component of the cochlear implant may be via a wired or wireless connection. In such embodiments, the process may be initiated by a command (e.g., initiated by the surgeon) being transmitted from the external device to the control circuit 402 to initiate the process. A further description of exemplary external devices is provided below.

In another embodiment, the external device may be directly connected to the leads connected to the electrode(s), such as, for example, in embodiments in which the stimulating lead assembly is implanted prior to connecting the stimulating lead assembly to the stimulator unit. In such embodiments, the control circuit 402, signal generator 404, resistor 406, and voltage measurement circuit 408 may be implemented in the external device.

Or, for example, in embodiments in which the process is performed after surgical implantation of the stimulating lead assembly, a clinician may connect to the sound processing unit 126 and direct sound processing unit 126 to send a command to the stimulator unit 420 to initiate the process. In another embodiment, control circuit 402 may, for example, determine to initiate the process based on an amount of time that has elapsed since the last measurement (e.g., the control circuit 402 performs measurements once a day, week, month, etc.). Or, for example, control circuit 402 may monitor performance of the stimulator unit 420 and initiate the process if a particular event occurs (e.g., a fault is detected).

In the presently discussed embodiment, at block 504, control circuit 402 selects the first pair of electrodes 448 and 450 for which impedance measurements are to be taken. The selected pair of electrodes 448 and 450 may be a pair of electrodes that is used for application of stimulation via monopolar stimulation, where current flows from an electrode 448 of the stimulating lead assembly to an extra-cochlear electrode 450. Or, for example, (e.g., in systems that use bipolar stimulation) both electrodes of the pair may be electrodes of the stimulating lead assembly.

In an embodiment, the stimulating lead assembly comprises 22 electrodes, where each electrode is paired with the extra-cochlear electrode to provide 22 separate stimulation channels. In one such embodiment, control circuit 402 performs impedance measurements for each of the 22 separate stimulation channels using the electrode pairs corresponding to each stimulation channel. Control circuit 402 may select, for example, a pair of electrodes corresponding to one of these stimulation channels as the first selected pair of electrodes and then in subsequent passes, control circuit 402 may select the electrode pairs for the other stimulation channels.

For each selected electrode pair, control circuit 402 takes impedance measurements for a plurality of frequencies. In an embodiment, these frequencies are spaced across the operational frequency range of the device. However, in other embodiments, the frequencies may include frequencies outside the normal operation range of the device.

The frequency of the applied sinusoidal voltage may be swept from low to high or high to low in a number of steps and measurements of the sinusoidal current amplitude and phase taken at each frequency step. For example, in a system where the operation frequency range is between 50 and 20 kHz (i.e., a frequency sweep ranging from 50-20 kHz), control circuit 402 may take measurements at 200 logarithmic steps along the frequency range. The frequency range for which measurements are to be taken may vary depending on the specifics of the embodiment but is typically over many orders of magnitude (e.g. 50-20 kHz, 10 mHz to 1 MHz, etc.)

In another embodiment the current is applied at the selected frequency and the voltage is measured. In this case block 508 in FIG. 5 would read "Apply current at selected frequency" and block 510 in FIG. 5 would read "Measure voltage".

In another embodiment the applied voltage signal is not of a single frequency but comprises the sum of a plurality of frequencies. Since the response properties of tissue for small voltage perturbations can be considered linear the recorded current will then contain signals at the same frequencies as those in the stimulating voltage waveform. These frequencies can be separated with appropriate filtering to yield the same information as if individual frequencies had been applied and measured sequentially as illustrated in FIG. 5. This method has the advantage that it may be quicker to perform than the method described in FIG. 5 since all frequencies are applied simultaneously. It has the disadvantage that it may be less accurate than the method described in FIG. 5 due to the additional filtering step.

Blocks 506-512 illustrate a simplified method of applying a frequency sweep and performing measurements for a selected electrode pair. It should, however, be understood that other mechanisms for applying a frequency sweep and obtaining measurements may be used. Further, the voltages, number of measurements and frequency range of the sweep are exemplary only, and in other embodiments different values may be used.

At block 506, control circuit 402 selects the starting frequency (e.g., 50 Hz) and voltage for the sweep (e.g., 50 mV). At block 508, control circuit 402 directs signal generator 404 to begin the frequency sweep. In response, signal generator 404 applies a signal to the electrodes at the specified frequency and voltage. The voltage selected at block 506 is preferably fairly small (e.g. 50 mV) so that the Voltage/Current (V/I) characteristic for the medium to be measured can be considered linear over the voltage range of the applied sinusoidal signal. Further, in an embodiment, the selected voltage may be a sub-threshold voltage, so that a hearing percept is not caused by the applied signal and the recipient may be unaware that the measurements are taking place. The signal applied by signal generator 404 to electrodes 448 and 450 may be a fixed sinusoidal signal at the specified frequency and voltage.

As noted above, resistor 406 is in series with signal generator 404, electrode 448, the recipient's tissue 452, and electrode 450. Thus, the current through resistor 406 corresponds to the current passing through electrodes 448 and 450. Control circuit 402 measures the current through the electrodes 448 and 450 at block 510. This measurement may include both the amplitude and phase of the current. In the illustrated embodiment, voltage measurement circuit 408 measures the voltage drop across resistor 406 and provides the measured voltage to control circuit 402, which converts the measured voltage to current using the formula: I=V/R, where I is the measured current, V is the measured voltage, and R is the resistance of resistor 406. Further, the measured currents (or voltages) can be converted to a total impedance for the electrodes 448 and 450 and tissue 452 using the following formula: $V_{tot}=V_R+I*R_{tot}$, where $V_{tot}$ is the voltage supplied by signal generator 404, $V_R$ is the voltage drop across resistor 406, I is the measured current through resistor 406, and $R_{tot}$ is the total impedance of electrodes 448 and 450 and tissue 452. This formula can be rewritten as $R_{tot}=(V_{tot}-V_r)/I$. Further, the measured voltages, currents, and impedances may be complex comprising real and imaginary parts based on the measured amplitudes and phases.

Control circuit 402 determines if the frequency sweep is completed or not at decision 512. If not, control circuit 402 increases the frequency of signal generator 404 at block 514. As noted above, in an embodiment, the frequency sweep may range from 50 Hz to 20 kHz, with the control circuit taking 200 measurements logarithmically spaced between 50 Hz and 20 kHz. Thus, in an embodiment, control circuit 402 may direct the signal generator 404 to apply a signal at the next frequency (e.g., 51.5 Hz, 53.1 Hz, ... 19409.8 Hz, 20 kHz) for which the control circuit 402 is to obtain a measurement.

Once the frequency sweep is completed and the measurements obtained, the control circuit 402 determines, at decision 516, if measurements are to be obtained for other electrode pairs. For example, in an embodiment, control circuit 402 obtains measurements for each electrode (paired with the extra-cochlear electrode) of the cochlear implant. However, in embodiments, control circuit 402 only obtains measurements for a subset of the electrodes.

If measurements are to be obtained for other electrode pairs, the process returns to block 504 and measurements are obtained for the next electrode pair. Once measurements are obtained for each electrode pair to be measured, the process proceeds to block 518 and measurements are analyzed. The particulars of this analysis may vary depending on the particular information sought. Exemplary mechanisms for analyzing and using this data (e.g., presenting location information to a surgeon) are discussed below.

Figure 6A:
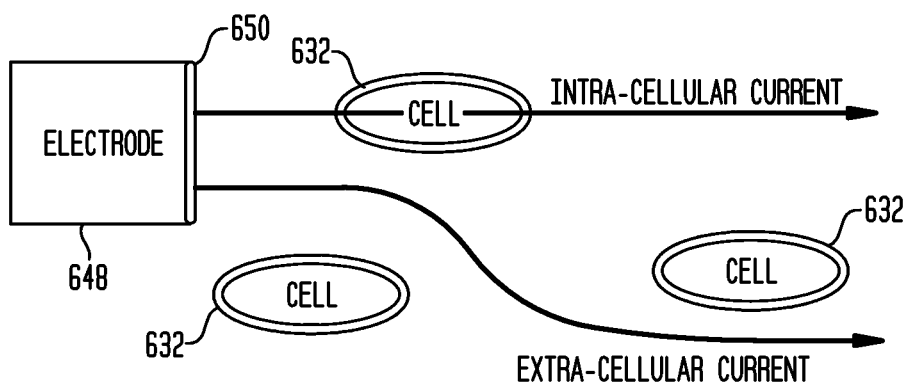
FIG. 6A illustrates a platinum electrode surrounded by a cellular medium (i.e. tissue)
Figure 6B:
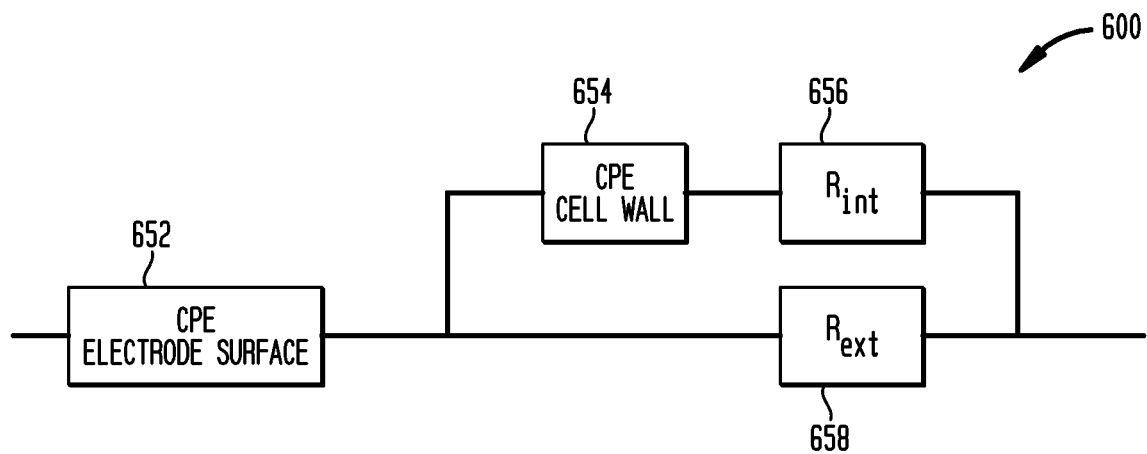
FIG. 6B illustrates an equivalent circuit model 600 of the system illustrated in FIG. 6A.

FIG. 6A illustrates a platinum electrode surrounded by a cellular medium (i.e. tissue). FIG. 6A is provided to illustrate how impedance spectroscopy can be used to determine the properties of the medium surrounding the electrode. FIG. 6B illustrates an equivalent circuit model 600 of the system illustrated in FIG. 6A. As shown in FIG. 6B the equivalent circuit model 600 includes Constant Phase Elements (CPEs) 652 and 654 that are used to describe the circuit properties of biological interfaces, which are typically rough or non-uniform at the microscopic level. A description of the CPE circuit model will be discussed below with reference to FIGS. 7A-7B.

As shown in FIG. 6A, current from the electrode 648 (e.g., an electrode 148 (FIG. 1)) travels from the electrode's surface 650 through the tissue via two paths: an intracellular path where the current passes through cells 632 of the tissue and an extra-cellular current path where the current travels around the cells 632.

As noted the electrode's surface 650 is non-uniform at the microscopic level and can be modeled as a CPE 652. Similarly, the walls of the cells 632 may be modeled as a CPE 654. The resistance of the intra-cellular current path is modeled as resistive element, $R_{int}$ 656. The resistance of the extra-cellular path is modeled as resistive element, $R_{ext}$ 658.

FIG. 7A provides a diagram for illustrating how the uneven surface of an electrode at the microscopic level can be modeled as a CPE. As shown, the electrode surface 702 may have one or more microscopic pores 704 and the surface can be modeled as an imperfect capacitor.

FIG. 7B provides a diagram of a circuit model for a CPE in accordance with FIG. 7A. The circuit model uses conventional electrical components and comprises a plurality of arms, each with a resistor 712 and a capacitor 714. The resistance and capacitance of each arm increase by a factor of N (e.g., N=2) for each arm of the circuit. The circuit model includes enough arms so that the RC time constants for the circuit span the frequency range being modeled. The CPE can be viewed as a circuit element whose phase angle (angular difference between the phase of the voltage sinusoid and the current sinusoid) remains the same, regardless of the frequency applied to it. In an embodiment, the phase angle is such that the current leads the voltage by around 45 degrees.

As noted above with reference to FIGS. 4-5, the data recorded for each electrode pair is in the form of the amplitude and phase of a sinusoid resulting from the applied signal. This data can also be represented as real and imaginary parts of the complex impedance of the electrodes 448 and 450 and tissue 452 (FIG. 4). This data can be plotted in a number of ways, each highlighting different features of the medium being tested. For example, the data can be plotted with the magnitude of the impedance on the y-axis against frequency on the x-axis.

Figure 8:
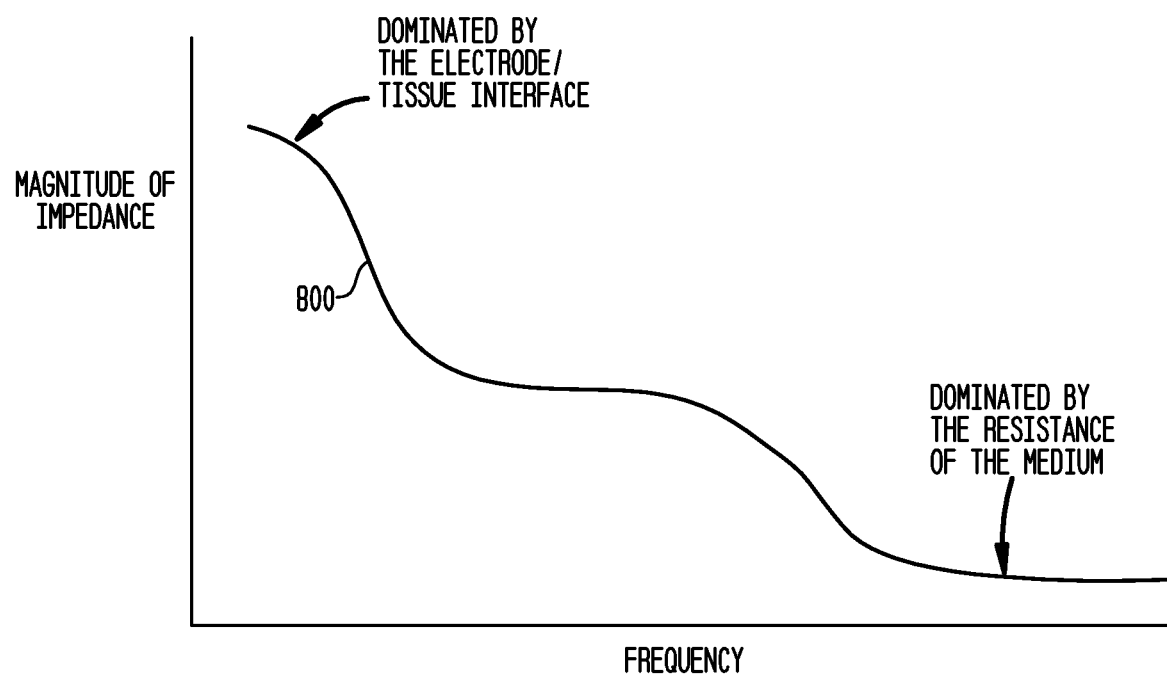
FIG. 8 is an exemplary plot for an electrode surrounded by a cellular medium, such as shown in FIG. 6A.

FIG. 8 is an exemplary plot for an electrode surrounded by a cellular medium, such as shown in FIG. 6A. FIG. 8 provides a curve 800 of the measured impedance amplitudes versus frequency for one of the measured electrodes 458 of the stimulating lead assembly. In the model of FIGS. 6A-6B, at extremely high frequencies the CPEs 652 and 654 all have very low impedance so the total impedance of the circuit becomes the parallel combination of $R_{int}$ and $R_{ext}$. Hence, above a certain frequency, the system looks completely resistive. At very low frequencies the CPEs 652 and 654 (representing the platinum/tissue interfaces) dominate the system and the magnitude of the interface CPEs 652 and 654 can be determined. The bumps in the curve 800 at intermediate frequencies are caused by the presence of the cells and cell walls in the medium. Different cell types cause different inflections and plateaus in this intermediate region of the plot. Thus, obtaining impedance measurements for plurality of frequencies, as shown, helps provide a mechanism for distinguishing between impedances due to the electrode and those due to the tissue.

In embodiments, the selected set of frequencies to be measured can be tailored to the particular application. For example, the typical time taken to run a full impedance sweep can be several minutes or hours since typically the frequencies in the milli-Hertz region require long data collection times. Since these low frequency measurements provide information mostly about the electrode/tissue interface and not its surrounding structures, in certain embodiments (e.g., when used during cochlear implant implantation), the method can omit many of the low frequency measurements. For example, when used during cochlear implantation, the method may only take measurements for a subset of key frequencies that can be quickly obtained and provide sufficient information for identifying the location of the stimulating lead assembly.

In the above discussed embodiment of FIG. 4, a dedicated signal generator 404 (FIG. 4) was used for applying the signal to the electrode pair. This dedicated signal generator circuitry may be useful in forcing a sinusoidal voltage or current and measuring a resulting sinusoidal current or voltage, respectively.

In other embodiments, the stimulating signal generation circuitry used for applying stimulation to a recipient in an implantable stimulator system may be used to generate the signal(s) used to measure impedance. For example, cochlear implants typically include circuitry designed to deliver a square wave current pulse as part of their neural stimulator function. Existing cochlear implants also typically include circuitry for measuring a voltage drop across the electrodes (e.g., the voltage drop across a particular electrode and the extra-cochlear electrode or the voltage drop across two electrodes of the stimulating lead assembly). Embodiments of the present invention use the square wave current pulse of the signal generation circuitry to obtain impedance spectroscopy data by measuring and storing the voltage across the electrodes (e.g., the electrode of the stimulating lead assembly that applied the pulse and the extra-cochlear electrode) at various times during the pulse.

FIG. 9 illustrates a square wave current pulse 902 and a resulting measured voltage 904, in accordance with an embodiment of the present invention. In this embodiment, the stimulating signal generation circuitry of the cochlear implant is used to apply the current pulse. Further, circuitry included in the stimulator unit is used to measure the voltage across the electrode pair. Although data obtained in this manner may not be exactly translated into the data obtained through conventional impedance spectroscopy, it is closely related to it and is likely to provide useful information for deriving information about the structures near the electrodes.

In an embodiment, the time during the pulse at which the voltage across the electrodes is measured is closely related to the inverse of the frequency in a conventional impedance spectroscopy system. For example, the voltage measured 10 μs after the start of the current pulse is closely related to the amplitude data that would be obtained at a frequency of 100 kHz (=1/10 μs) with a conventional impedance spectroscopy system. Similarly, voltage measured 100 μs after the start of a pulse is closely related to an impedance spectroscopy amplitude measured at a frequency of 10 kHz=1/100 μs.

The Laplace transform can be used to relate the measured voltage during the stimulation pulse to the frequency spectrogram as follows: During (phase 1 of) a constant current stimulation pulse, assume the time domain current is I(t) and the time domain voltage is V(t). I(t) and V(t) can be transformed using the Laplace operator to yield the frequency domain current, I(s), and frequency domain voltage, V(s) as follows.

For a constant current stimulator I(t)=I (a constant) so the frequency domain current, I(s) is the Laplace transform of the constant I so: I(s)=I/s. The signal V(t) is measured numerically by the AIMD. The Laplace transform, V(s), of the time domain voltage waveform, V(t), can be calculated numerically from the measured values of time domain voltage, V(t). i.e.: V(s)=L[V(t)] where L is the Laplace operator.

From the frequency domain current, I(s), and the frequency domain voltage, V(s), the frequency domain impedance, also known as the impedance spectrogram, can be calculated as: Z(s)=V(s)/I(s). As noted above, the measured impedance data may be analyzed in various manners depending on the particular implementation. For example, in an embodiment, the raw current measurements may be provided by control circuit 402 (FIG. 4) to an external device that analyzes the measurements to display information to a surgeon regarding the location of the stimulating lead assembly. This external device may be, for example, a computer or specialized piece of hardware and/or software. Or, for example, in an embodiment, the data is analyzed by cochlear implant 100, such as by the sound processor 126 or control unit 402. The cochlear implant 100 may analyze the data to, for example, determine if a fault occurred or the stimulating lead assembly has shifted position from its initial position. The cochlear implant (e.g., sound processor 126) may then take appropriate action such as, for example, modifying the MAP used in generating electrical stimulation, providing an indication to the external speech processor that can be used to notify the recipient or surgeon of an issue with the cochlear implant, or, for example, terminate the application of stimulation to the recipient.

As noted, in an embodiment, control circuit 402 provides the raw data to an external device, such as a computer or specialized piece of hardware that analyzes the data. In such an embodiment, the external device may be connected to the sound processor 126 (FIG. 1) by a wired or wireless connection. For example, in an embodiment, control circuit 402 provides the data to internal receiver unit 132 (FIG. 1), which transmits the data to external transmitter unit 128. External transmitter unit 128 then provides the data to sound processor 126, which then provides the data to the external device.

The external device may compute a curve, such as curve 800, from the raw data and compare the computed curve to known curve patterns representing different characteristics to identify the proximity of the electrode to a particular structure. Various techniques may be employed for performing this comparison, such as, for example, by using a neural network to compare the measured curve to known curve patterns to determine the proximity of the electrode to different structures. For example, the curve shape for an electrode close to the modiolus will be different than the curve shape for an electrode that is located away from the modiolus and surrounded by perilymph.

The following provides an exemplary description of an embodiment in which the measured information is provided to an external device so that information on the location of the stimulating lead assembly may be presented to a surgeon during implantation of the stimulation lead assembly. In an embodiment, this information is provided in real time so that a surgeon implanting a stimulating lead assembly can obtain real time data about the cochlear structures near the stimulating lead assembly. This information may be displayed to the surgeon in a visual form (for example a head up display of one or more of the impedance spectroscopy plots). Or, for example, this visual data may be presented through the operating microscope as a head-up display. Or, for example, the data may be presented aurally as a single frequency continuous tone (e.g. the tone frequency or amplitude could be related to the impedance spectroscopy amplitude data measured at a particular frequency). Or the sound could be a continuous, complex sound (e.g. consisting of a summation of multiple tones, each tone related to the impedance spectroscopy amplitude at a range of frequencies). Or the sound could be a series of tone bursts where the tone burst frequency is related in some way to the salient impedance spectroscopy data.

As noted, in embodiments the data is presented in real time (so the tone or visual data changes more or less instantaneously as the stimulating lead assembly is moved) or it may be presented after the fact. The advantage of real time is that it allows the surgeon to respond instantly to any detected changes or problems associated with the proximity to neural structures. The advantages of "after the fact" presentation is that it allows more time for any post processing of data that may be necessary in order to extract the most useful data to present to the surgeon.

The data processing, salient feature extraction and presentation means will vary depending on the application required. For example, if a surgeon wishes to know the proximity of all the electrodes of a cochlear implant stimulating lead assembly to the lateral wall of the cochlea, then, in an embodiment, data from all the electrodes of the array are measured, processed and presented to he surgeon, in more or less real time.

In another embodiment, a clinician may wish to determine, postoperatively, the proximity of the electrodes of a stimulating lead assembly to the modiolus. This may provide useful data that affects the way the cochlear implant is programmed (e.g. there is evidence to show that close modiolar positioning of the electrodes reduces current spread and potentially allows the use of programming strategies requiring greater spatial selectivity). In this case there is no need for real time processing of the data since the clinician has ample to time to consider the best way to program the cochlear implant. In this case it may be advantageous to do more complex processing and presentation of the impedance spectroscopy data, perhaps presenting the data in a range of presentation styles and methods, since additional information relevant to modiolar proximity may be obtained through greater processing of the raw data.

In addition to plotting the measured impedance amplitudes versus frequency and comparing the plot to known patterns, embodiments of the present invention may also analyze the data in different ways depending on the particular physical characteristics of the cells or electrode that are to be determined. These other mechanism include, for example, plotting (a) the phase angle of the complex impedance vs. frequency; (b) the real component of the complex impedance vs. frequency; (c) the imaginary component of the complex impedance vs. frequency; and (d) the real (e.g., x-axis) vs. imaginary (y-axis) impedance components for each frequency measured. Further, in another embodiment, rather than simply using the raw data, the data may be further processed. For example, in an embodiment, the derivative of the measured impedance (or voltage or current) vs. time is obtained and the resulting derivative is used, for example, to obtain information regarding the stimulating lead assembly, such as information regarding the proximity of the electrode to the structure of the medium surrounding the tissue. In one such embodiment, the resulting derivative values are plotted versus frequency and displayed to the surgeon, or for example, used as inputs to a classification algorithm (e.g., neural network) such as discussed above.

In an embodiment, the impedance spectroscopy data may be combined (e.g., by an external device) with other data relating to structures near the electrode (e.g., x-rays and other imaging data, optical measurements, force measurements, etc.).

It should be noted that the above description provides one example for obtaining impedance spectroscopy measurements, and in other embodiments, more complex impedance spectroscopy measurements may be obtained. For example, in the embodiment the current is measured on the same electrode as the one that applies the voltage. It is also possible to apply current or voltage on one electrode and measure voltage or current respectively on one or more other electrodes in the array of electrodes. Applying voltage or current on one electrode and measuring the voltage or current on another electrode is known to those of skill in the art and is not discussed further herein. The system of forcing current on one electrode and then measuring voltage on other electrodes in an array of electrodes is sometimes referred to as electrode field imaging.

As noted above, impedance spectroscopy data may be used for determining proximity information. Additionally, as noted above, the impedance spectroscopy data may be used for obtaining other types of information. For example, the impedance spectroscopy data may be used to determine if tip fold over occurs during surgical implantation of a stimulating lead assembly. When tip fold-over occurs, the electrode spacing is changed, such that one or more electrodes may be located very near another electrode. In embodiments in which impedance spectroscopy data is used to detect tip fold over, a current or voltage may be applied on one or more electrodes and measured on one or more different electrodes. If tip fold over occurs the current or voltage applied on the electrode(s) may be received on the other electrode(s) with a resulting distinctive profile that may be used to detect tip fold over. In such an embodiment, a classification algorithm (e.g., a neural network) may be used to determine if the measured values indicate that tip fold over has occurred.

In another embodiment, the impedance spectroscopy data is used to detect whether there is a fault or whether the tissue includes diseased or damaged cells. In such an embodiment, these faults, as well as issues with the tissue may each have distinctive impedance spectroscopy characteristics. In an embodiment, a classification algorithm (e.g., neural network) may be used to analyze the measured impedance spectroscopy data to determine if any of these issues has occurred.

In another embodiment, impedance spectroscopy measurements are obtained using a four point impedance method. In this method the voltage between two nearby electrodes is measured while passing current between two other electrodes flanking the measurement electrodes. A further description of an exemplary four point impedance method is provided in U.S. Patent Publication No. 2011/0087085 entitled "Method and Device for Intracochlea Impedance Measurements."

Reference herein to "one embodiment" or "an embodiment" means that a particular feature, structure, operation, or other characteristic described in connection with the embodiment may be included in at least one implementation of the invention. However, the appearance of the phrase "in one embodiment" or "in an embodiment" in various places in the specification does not necessarily refer to the same embodiment. It is further envisioned that a skilled person could use any or all of the above embodiments in any compatible combination or permutation.

It is to be understood that the detailed description and specific examples, while indicating embodiments of the present invention, are given by way of illustration and not limitation. Many changes and modifications within the scope of the present invention may be made without departing from the spirit thereof, and the invention includes all such modifications.

What is claimed is:

1. A method of operating an active implantable medical device (AIMD) that is a cochlear implant comprising at least one electrode, the cochlear implant being configured to execute an impedance spectroscopy method, the method comprising:
    applying a measurement signal at a plurality of frequencies to a recipient of the AIMD using the electrode;
    performing, using the AIMD, a measurement, responsive to the measurement signal and indicative of an impedance of the electrode and tissue of the recipient, at each of the plurality of frequencies;
    analyzing the measurements to obtain information regarding the proximity of the electrode to one or more tissue structures inside a cochlea; and
    at least one of:
        assessing an extent of scar tissue around the electrode based on the measurements;
        determining a presence of an infection proximate the electrode based on the measurements; or
        determining, based on the measurements, a complication associated with the electrode.

2. The method of claim 1, further comprising:
    analyzing the measurements to determine location information regarding the electrode.

3. The method of claim 1, wherein the analyzing comprises:
    analyzing the measurements to determine information regarding a proximity of the electrode to one or more tissue structures.

4. The method of claim 3, wherein the one or more tissue structures comprise a modiolus.

5. The method of claim 1, wherein the analyzing is performed during implantation of a component of the AIMD, wherein the component comprises the electrode.

6. The method of claim 5, further comprising displaying on a device external to the AIMD the location information during the implantation.

7. The method of claim 6, where the displaying comprises:
    displaying the information on a heads-up display.

8. The method of claim 1, wherein:
    the action of applying a measurement signal includes
        applying a first measurement signal at a first of the plurality of frequencies with a specified electrical characteristic using the electrode;
    the method further comprises:
        applying a second measurement signal at a second of the plurality of frequencies with the specified electrical characteristic using the electrode, wherein
    the action of performing a measurement includes:
        measuring a first impedance of the electrode and tissue in response to the first measurement signal at the first of the plurality of frequencies; and
        measuring a second impedance of the electrode and tissue in response to the second measurement signal at the second of the plurality of frequencies.

9. The method of claim 8, further comprising:
    computing a curve using the first and second impedances; and
    comparing the computed curve to one or more known curve patterns to identify the proximity of the electrode to one or more tissue structures.

10. The method of claim 9, wherein comparing comprises:
    using a neural network in comparing the computed curve to one or more known curve patterns.

11. The method of claim 1, wherein the measurement signal is applied by a signal generator of the AIMD implanted in the recipient that is configurable to apply at least one stimulation signal using the electrode to cause a hearing percept by the recipient.

12. The method of claim 1, wherein the cochlear implant comprises an extra-cochlear electrode and a stimulating lead assembly comprising the electrode and a plurality of other electrodes, wherein
    the applying comprises:
        applying the measurement signal using the electrode and the extra-cochlear electrode; and
    wherein the method further comprises:
        applying a second measurement signal at a plurality of frequencies to the recipient using one of the plurality of other electrodes and the extra-cochlea electrode; and
        performing, using the AIMD, a second measurement responsive to the second measurement signal and indicative of an impedance of the one of the plurality of other electrodes and tissue of the recipient, at each of the plurality of frequencies.

13. The method of claim 1, where the applying and performing are performed for each of the plurality of frequencies using a frequency sweep.

14. The method of claim 13, wherein the plurality of frequencies of the frequency sweep comprise frequencies logarithmically spaced across a frequency range of the frequency sweep.

15. The method of claim 1, further comprising:
    adjusting one or more operating parameters of the AIMD based on the measurements.

16. The method of claim 1, further comprising:
    emitting an audible signal based on the analysis.

17. The method of claim 1, wherein:
    the AIMD includes a plurality of separate stimulation channels; and
    the method includes performing at least one of impedance measurements or voltage measurements for the plurality of channels using respective different electrode pairs corresponding to respective channels, and
    for each respective pair, at least one of impedance measurements or voltage measurements are taken for a plurality of frequencies.

18. The method of claim 1, further comprising:
    evaluating the measurements to differentiate between different physical structures in the recipient that have different spectroscopic signatures, wherein the AIMD is implanted in a head of a recipient with the electrode in the cochlea.

19. The method of claim 1, wherein:
    the AIMD includes a stimulating lead assembly; and
    the method further comprises determining an instantaneous insertion depth of the stimulating lead assembly in a cochlea the cochlea of the recipient.

20. The method of claim 1, further comprising at least one of:
  assessing the extent of scar tissue around the electrode based on the measurements; or
  determining the presence of an infection proximate the electrode based on the measurements.

21. The method of claim 1, wherein:
  the AIMD includes an electrode array having a tip inserted into the cochlea of the recipient; and
  the method further comprises determining whether the tip of the electrode array is in a fold-over state based on a distinctive data related to the measurements indicative of such a fold-over state.

22. The method of claim 21, further comprising:
  utilizing a classification algorithm to determine whether the tip of the electrode array is in a fold-over state.

23. The method of claim 1, wherein:
  the applying action and the performing action are executed during surgical implantation of the AIMD.

24. The method of claim 1, further comprising assessing the extent of scar tissue around the electrode based on the measurements, wherein the electrode is located in the cochlea of the recipient.

25. The method of claim 1, further comprising:
  distinguishing between impedances due to the electrode and impedances due to the tissue.

26. The method of claim 1, further comprising:
  determining a magnitude of an impedance at an interface between the electrode and the tissue.

27. The method of claim 1, further comprising:
  determining a first magnitude of a first impedance at a first interface between the electrode and the tissue; and
  determining a second magnitude of a second impedance at a second interface between another electrode different than the electrode of the first interface and the tissue.

28. The method of claim 1, further comprising:
  evaluating at least one of a position of the electrode or a tissue quality of the tissue based on the measurements by taking into account the influence of the impedance of the electrode as compared to the impedance of the tissue on the measurements.

29. The method of claim 1, further comprising:
  analyzing the measurements and predicting performance of the AIMD based on the measurements.

30. The method of claim 1, further comprising:
  surgically implanting a cochlear electrode array into the cochlea based on the measurements.

31. The method of claim 13, wherein:
  at least one of:
    the frequency sweep includes taking a plurality of steps along the frequency range;
    the frequency sweep includes taking a plurality of logarithmic steps along the frequency range; or
    the frequency sweep includes skipping at least 199 frequencies between 50 Hz and 20 kHz; and
  making one or more adjustments associated with the AIMD based on the measurements.

32. The method of claim 1, wherein:
  the method further comprises displaying on a device external to the AIMD information about the measurements and adjusting one or more operating parameters of the AIMD based on the measurements; and
  the action of displaying on the device external to the AIMD information about the measurements to a person is executed through an operating microscope.

33. The method of claim 29, wherein:
  the action of applying a measurement signal at a plurality of frequencies to a recipient of the AIMD using the electrode includes taking a plurality of steps along the frequency range.

34. The method of claim 1, further comprising: analyzing the measurement to determine a fault regarding the AIMD, wherein: the fault is a fault that is more complex than simple open circuits or short circuits.

35. The method of claim 1, wherein:
  an action of displaying on the device external to the AIMD information about the measurements to a person is displayed to a surgeon implanting the AIMD in real time with respect to the implantation.

36. The method of claim 1, wherein:
  the method further comprises making one or more adjustments associated with the AIMD based on the measurements; and
  the action of applying a measurement signal at a plurality of frequencies to a recipient of the AIMD using the electrode includes skipping at least 199 frequencies between 50 Hz and 20 kHz.

37. The method of claim 1, wherein:
  the method further comprises making one or more adjustments associated with the AIMD based on the measurements; and
  the action of applying a measurement signal at a plurality of frequencies to a recipient of the AIMD using the electrode includes taking a plurality of logarithmic steps along an operational frequency range of the AIMD.

38. The method of claim 1, wherein:
  the method further comprises making one or more adjustments associated with the AIMD based on the measurements; and
  the action of applying a measurement signal at each of the plurality of frequencies is executed without causing a hearing percept.

39. The method of claim 1, wherein:
  the method further comprises making one or more adjustments associated with the AIMD based on the measurements; and
  the action of applying a measurement signal at each of the plurality of frequencies is executed during a surgical implantation operation of the AIMD.

40. The method of claim 1, wherein the cochlear implant comprises an extra-cochlear electrode and a stimulating lead assembly comprising the electrode and a plurality of other electrodes located in the cochlea, and wherein the measurement signal does not cause a hearing percept in the recipient.

41. The method of claim 1, wherein the tissue is tissue of the cochlea.

42. The method of claim 1, wherein the cochlear implant comprises an extra-cochlear electrode and a stimulating lead assembly comprising the electrode and a plurality of other electrodes located in the cochlea, and wherein the measurement signal causes a hearing percept in the recipient.

43. The method of claim 1, wherein the analyzing is performed during implantation of a component of the AIMD, wherein the component comprises the electrode, and wherein the method further comprises providing data to a surgeon indicative of a state of the AIMD during implantation thereof, which data is based on the measurements.

44. The method of claim 29, wherein:
  the measurements is indicative of proximity of the electrode to a modiolus, and wherein the AIMD is the cochlear implant.

45. The method of claim 28, wherein:
the action of evaluating at least one of a position of the electrode or a tissue quality of the tissue based on the measurements by taking into account the influence of the impedance of the electrode as compared to the impedance of the tissue on the measurements includes evaluating the position of the electrode based on the measurements by taking into account the influence of the impedance of the electrode as compared to the impedance of the tissue on the measurements.

46. The method of claim 38, wherein the electrode is proximate tissue structure, wherein the tissue structure comprises tissue of the cochlea.

47. The method of claim 1, further comprising determining the presence of an infection proximate the electrode based on the measurements.

48. The method of claim 1, further comprising determining, based on the measurements, the complication associated with the electrode.

* * * * *